United States Patent
Conde et al.

(10) Patent No.: US 9,243,003 B2
(45) Date of Patent: Jan. 26, 2016

(54) PROCESS FOR PREPARING BENZOXABOROLES

(75) Inventors: Jose J. Conde, King of Prussia, PA (US); John Anthony Kowalski, King of Prussia, PA (US); Matthew Allen Zajac, King of Prussia, PA (US)

(73) Assignee: GlaxoSmithKline LLC, Philadelphia, PA (US)

(*) Notice: Subject to any disclaimer, the term of this patent is extended or adjusted under 35 U.S.C. 154(b) by 242 days.

(21) Appl. No.: 13/639,594

(22) PCT Filed: Apr. 6, 2011

(86) PCT No.: PCT/US2011/031384
§ 371 (c)(1),
(2), (4) Date: Oct. 5, 2012

(87) PCT Pub. No.: WO2011/127143
PCT Pub. Date: Oct. 13, 2011

(65) Prior Publication Data
US 2013/0035501 A1    Feb. 7, 2013

Related U.S. Application Data

(60) Provisional application No. 61/321,642, filed on Apr. 7, 2010.

(51) Int. Cl.
C07F 5/04 (2006.01)
C07F 5/02 (2006.01)

(52) U.S. Cl.
CPC .. C07F 5/025 (2013.01); C07F 5/04 (2013.01)

(58) Field of Classification Search
None
See application file for complete search history.

(56) References Cited

U.S. PATENT DOCUMENTS

| | | | |
|---|---|---|---|
| 7,205,425 | B2 | 4/2007 | Shibasaki et al. |
| 7,446,236 | B2 | 11/2008 | Naud et al. |
| 2009/0227541 | A1 | 9/2009 | Baker et al. |
| 2010/0048570 | A1 | 2/2010 | Kim et al. |

FOREIGN PATENT DOCUMENTS

WO    2006/096131    9/2006

OTHER PUBLICATIONS

Adamczyk-Wozniac, et al., Benzoxaboroles—Old compounds with new applications, J Organometallic Chem 694:3533-3541 (2009).

*Primary Examiner* — Alicia L Otton
(74) *Attorney, Agent, or Firm* — Barbara J. Carter

(57) ABSTRACT

The present invention is a process comprising contacting a compound of formula 6:

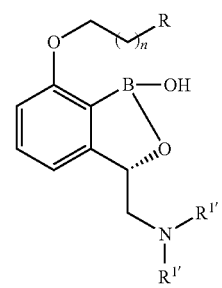

or a pharmaceutically acceptable salt thereof;
with a deprotecting reagent to form a compound of formula A:

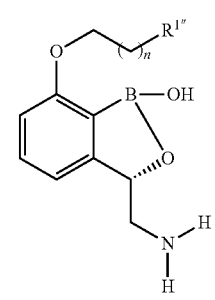

or a pharmaceutically acceptable salt thereof;
where R is H or OR$^1$; R$^1$ and each R$^{1'}$ are protecting groups; R$^{1''}$ is H or OH, and n is 0, 1, 2, 3, 4, or 5.

15 Claims, No Drawings

PROCESS FOR PREPARING BENZOXABOROLES

This application is filed pursuant to 35 U.S.C. §371 as a United States National Phase Application of International Patent Application Serial No. PCT/US2011/31384 filed Apr. 6, 2011, which claims priority to U.S. Provisional Application No. 61/321,642 filed Apr. 7, 2010; the contents of each of the foregoing applications are hereby incorporated by reference.

BACKGROUND OF THE INVENTION

The present invention relates to benzoxaboroles and methods for their preparation. The hydrochloride salt of (3S)-3-(aminomethyl)-7-[(3-hydroxypropyl)oxy]-2,1-benzoxaborol-1(3H)-ol, disclosed in U.S. patent application Ser. No. 12/142,692, now U.S. Pat. No. 7,816,344, is characterized by the following formula:

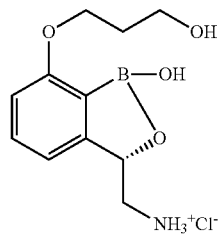

along with other pharmaceutically acceptable salts. These salts, as well as their corresponding conjugate free base, have shown promise as an antibacterial agent, especially against Gram negative pathogens. It would therefore be advantageous to discover alternative ways of preparing this agent and its salts.

SUMMARY OF THE INVENTION

In one aspect, the present invention is a process comprising deprotecting a compound of formula 6:

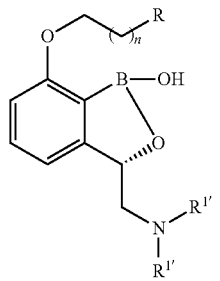

or a pharmaceutically acceptable salt thereof;
under deprotecting conditions to form a compound of formula A:

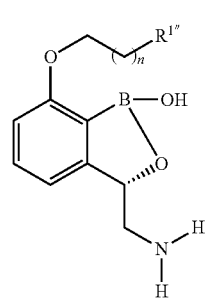

or a pharmaceutically acceptable salt thereof;

where R is H or OR$^{1}$; R$^{1}$ and each R$^{1'}$ are each protecting groups; R$^{1''}$ is H or OH; and n is 0, 1, 2, 3, 4 or 5.

In a second aspect, the present invention is a process comprising the steps of
a) contacting a compound of formula 2:

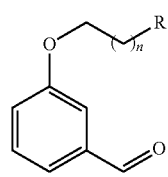

with nitromethane in the presence of a chiral reagent to make a compound of formula 3:

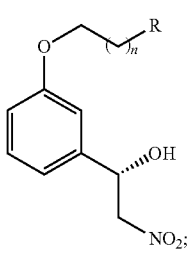

where R is H or OR$^{1}$; R$^{1}$ is a protecting group; and n is 0, 1, 2, 3, 4 or 5;
b) reducing the compound of formula 3 to form a compound of formula 4:

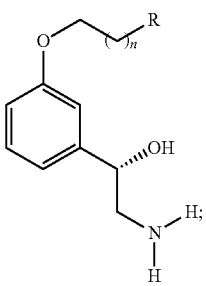

c) contacting the compound of formula 4 or a salt thereof with R$^{1'}$X with a base to form a compound of formula 5:

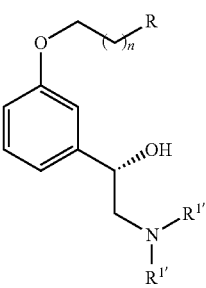

or a salt thereof, wherein $R^{1'}$ is a protecting group and X is a leaving group;

d) contacting the compound of formula 5 or a salt thereof with a borylating reagent characterized by the following formula:

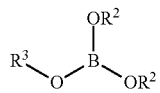

5 in the presence of n-BuLi to form a compound of formula 6:

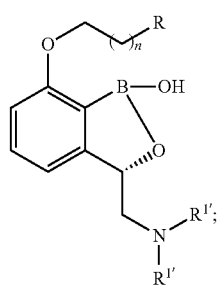

6 or a pharmaceutically acceptable salt thereof, where each $R^2$ is independently $C_1$-alkyl, $C_2$-alkyl, $C_3$-alkyl, $C_4$-alkyl, $C_5$-alkyl, $C_6$-alkyl, or together with the oxygen atoms to which they are attached form a 5- or 6-membered ring; and $R^3$ is $C_1$-alkyl, $C_2$-alkyl, $C_3$-alkyl, $C_4$-alkyl, $C_5$-alkyl, $C_6$-alkyl; and e) deprotecting the compound of formula 6 or a pharmaceutically acceptable salt thereof to form a compound of formula A or a pharmaceutically acceptable salt thereof:

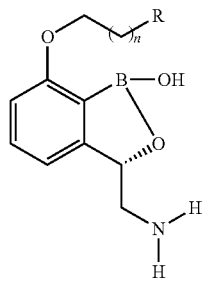

A where $R^{1'''}$ is H or OH.

In another aspect the present invention is a process comprising the steps of:

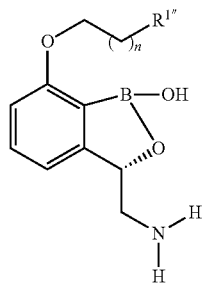

A a) brominating a compound of formula 8:
b) to form a compound of formula 9:

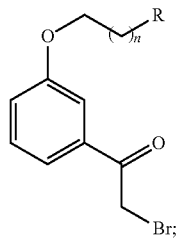

9 where R is H or $OR^1$; $R^1$ is a protecting group; and n is 0, 1, 2, 3, 4 or 5;

b) contacting the compound of formula 9 with $HN(R^{1'})_2$ to form a compound of formula 10:

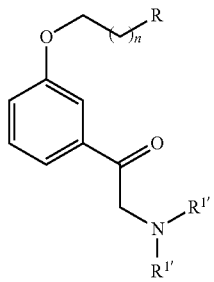

10 or a salt thereof, where each $R^{1'}$ is a protecting group;

c) enantioselectively reducing the compound of formula 10 to form a compound of formula 5:

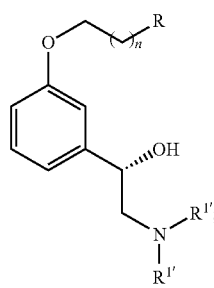

5 d) contacting the compound of formula 5 or a salt thereof with a borylating reagent characterized by the following formula:

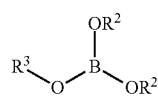

in the presence of n-BuLi, to form a compound of formula 6:

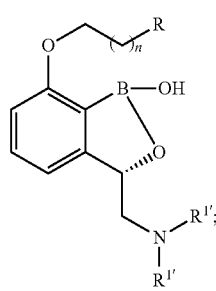

6 or a pharmaceutically acceptable salt thereof, where each $R^2$ is independently $C_1$-$C_6$-alkyl, or together with the oxygen atoms to which they are attached form [as above] a 5- or 6-membered ring; and $R^3$ is $C_1$-$C_6$-alkyl; and e) deprotecting the compound of formula 6 or a pharmaceutically acceptable salt thereof to form a compound of formula A or a pharmaceutically acceptable salt thereof:

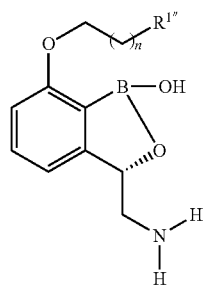
A where $R^{1'''}$ is H or OH.

In another aspect, the present invention is a compound characterized by the following formula 6a:

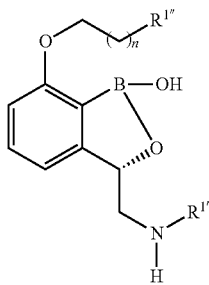
6a or a pharmaceutically acceptable salt thereof, where $R^{1'''}$ is H or OH; and $R^{1'}$ is a protecting group.

DETAILED DESCRIPTION OF THE INVENTION

In a first aspect, the present invention is a process comprising deprotecting a compound of formula 6:

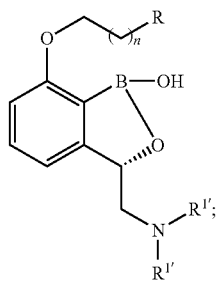
6 or a pharmaceutically acceptable salt thereof;
under deprotecting conditions to form a compound of formula A:

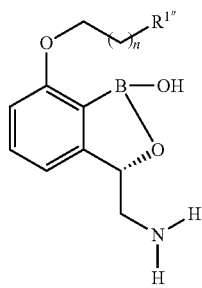
A or a pharmaceutically acceptable salt thereof;

where R is H or $OR^1$; $R^1$ and each $R^{1'}$ are protecting groups; $R^{1'''}$ is H or OH; and n is 0, 1, 2, 3, 4, or 5.

Examples of suitable $R^1$ protecting groups include —CH($R^a$)-phenyl-$(R^b)_x$, trialkylsilyl, tetrahydropyranyl, —CH$_2$OCH$_3$, or —CH$_2$OCH$_2$CH$_2$OCH$_3$ groups, where $R^a$ is H, $C_1$-alkyl, $C_2$-alkyl, $C_3$-alkyl, $C_4$-alkyl or phenyl; each $R^b$ is independently $C_1$-alkyloxy, $C_2$-alkyloxy, $C_3$-alkyloxy, $C_4$-alkyloxy; or $C_1$-alkyl, $C_2$-alkyl, $C_3$-alkyl, $C_4$-alkyl; and x is 0, 1, or 2. In another aspect, $R^1$ is benzyl.

$C_1$-$C_4$-alkyl refers to $C_1$-alkyl, $C_2$-alkyl, $C_3$-alkyl, $C_4$-alkyl, e.g. methyl, ethyl, n-propyl, isopropyl, n-butyl, sec-butyl, and t-butyl. Similarly, $C_1$-$C_4$-alkoxy refers to $C_1$-alkyloxy, $C_2$-alkyloxy, $C_3$-alkyloxy, $C_4$-alkyloxy e.g. methoxy, ethoxy, n-propoxy, isopropoxy, n-butoxy, sec-butoxy, and t-butoxy. $C_1$-$C_6$-alkyl refers to $C_1$-alkyl, $C_2$-alkyl, $C_3$-alkyl, $C_4$-alkyl, $C_5$-alkyl, $C_6$-alkyl.

Examples of suitable $R^{1'}$ protecting groups include —CH($R^b$)-phenyl-$(R^c)_y$; examples of such groups include benzyl, 1-phenylethyl, 2-methoxybenzyl, 3-methoxybenzyl, 4-methoxybenzyl, 2,4-dimethoxybenzyl, and diphenylmethyl groups; in another aspect, each $R^{1'}$ is benzyl.

Suitable deprotection methods include metal catalyzed hydrogenation, catalytic transfer hydrogenation, or acid cleavage. Where $R^{1'}$ is benzyl, preferred deprotection reagents include $H_2$ over Pd/C, $H_2$ over Pt/C, $H_2$ over palladium hydroxide, or ammonium formate and Pd/C.

In another aspect, n is 0, 1, 2 or 3; preferably, n is 2.

As used herein, "a pharmaceutically acceptable salt" refers to an acid addition salt. Examples of suitable acid addition salts are inorganic acid salts and organic salts; Examples of suitable inorganic salts include hydrochloric, hydrobromic, phosphoric, metaphosphoric, nitric, and sulfuric acid salts; examples of suitable organic acid salts include tartaric, acetic, trifluoroacetic, citric, malic, lactic, fumaric, benzoic, formic, propionic, glycolic, gluconic, maleic, succinic, methanesulfonic, ethanesulfonic, stearic, benzenesulfonic, bromobenzenesulfonic, and p-toluenesulfonic acid salts. The pharmaceutically acceptable salt of A is preferably an HCl salt.

In another aspect, the compound of formula 6 is reduced in the presence of HCl to form the hydrochloride salt of the compound of formula A.

In another aspect of the present invention, the compound of formula 6 is prepared by contacting a compound of formula 5:

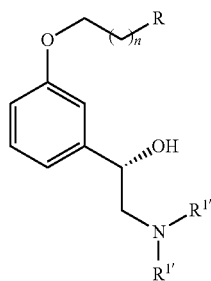

5 or a salt thereof with a borylating reagent in the presence of an alkyllithium such as n-BuLi, n-hexyllithium, or sec-BuLi.

The borylating reagent is characterized by the following formula:

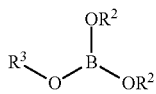

Each $R^2$ is independently $C_1$-alkyl, $C_2$-alkyl, $C_3$-alkyl, $C_4$-alkyl, $C_5$-alkyl, $C_6$-alkyl and each $R^3$ is $C_1$-alkyl, $C_2$-alkyl, $C_3$-alkyl, $C_4$-alkyl, $C_5$-alkyl, $C_6$-alkyl. Preferably, each $R^2$ is the same alkyl group; alternatively, the $R^2$ groups, together with the oxygen atoms to which they are attached form a 5- or 6-membered ring, which may be optionally fused to an aryl ring. Examples of suitable borylating reagents include isopropylpinacolborate, 2-(methoxy)-1,3,2-benzodioxaborole, and tri-$C_1$-borates, tri-$C_2$-borates and tri-$C_3$-borates such as triisopropyl borate and trimethyl borate. In another aspect, the borylating reagent is isopropylpinacolborate or trimethyl borate.

The compound of formula 5 or a salt thereof can be prepared by contacting under basic conditions $R^{1'}$X with a compound of formula 4:

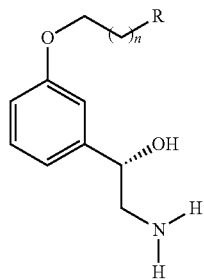

4 or a salt thereof, wherein X is a suitable leaving group such as a Br, Cl, I, tosyl, or triflyl group. Suitable bases include carbonates such as sodium potassium, and cesium carbonates, or hydroxides such as tetrabutylammonium hydroxide.

The compound of formula 4 or a salt thereof can be prepared by contacting a compound of formula 2:

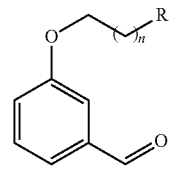

2 with nitromethane in the presence of a chiral reagent, to form a compound of formula 3:

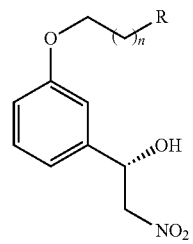

3 then reducing the nitro group to an amine group.

Examples of suitable chiral reagents include 1,7,7-trimethyl-N-(pyridin-2-ylmethyl)bicyclo[2.2.1] heptan-2-amine di-hydrochloride; (4S)-4-ethyl-2-{1-ethyl-1-[(4S)-4-(1-methylethyl)-4,5-dihydro-1,3-oxazol-2-yl]propyl}-4,5-dihydro-1,3-oxazole; (S)-4-(tert-butyl)-2-(2((S)-4-methyl-4,5-dihydrooxazol-2-yl)propan-2-yl)-4,5-dihydrooxazole; or N1,N2-bis[(1R,2R,4R)-1,7,7-trimethylbicyclo[2.2.1]hept-2-yl]-1,2-ethanediamine in the presence of a suitable catalyst such as Co(OAc)$_2$, Cu(OAc)$_2$, CuCl$_2$, Zn(OTf)$_2$, or Zn(Et)$_2$.

Examples of suitable nitro-reducing agents would include Pd/C, Pt/C or a mixture thereof, in the presence of hydrogen.

The compound of formula 2 is conveniently prepared by reaction of $R^1(CH_2)_3$—X with 3-hydroxybenzaldehyde in the presence of a suitable base, examples of which include hydroxide and carbonate bases.

Alternatively, the compound of formula 5 or a salt thereof can be prepared by enantioselective reduction of a compound of formula 10:

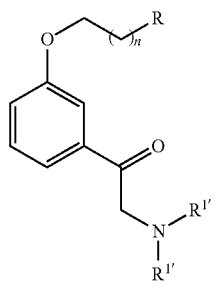

10 or a salt thereof.

Examples of an enantioselective reduction reagents include H$_2$ and ruthenium-, rhodium- or iridium-based catalyst such as (S)-2-[($S_p$)-2-(diphenylphosphino)ferrocenyl]-4-isopropyl-2-oxazoline triphenylphosphine ruthenium(II) dichloride complex (also known as Naud catalyst); (R)-BI- NAP-Ru—(R,R)-(+)-DPEN Cl (also known as Noyori catalyst), or oxazaborolidine-catalyzed borane reduction.

The compound of formula 10 or a salt thereof can be prepared by contacting $HN(R^{1'})_2$ with a compound of formula 9:

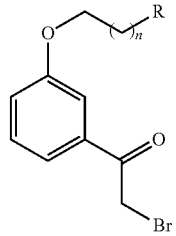

9

The compound of formula 9 can be prepared by bromination of a compound of formula 8:

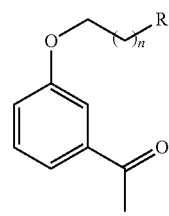

8

Suitable brominating reagents include $Br_2$ in dichloromethane, NBS, and tetra-n-butylammonium tribromide.

Compound 8 is prepared by contacting 3-hydroxyacetophenone with $X(CH_2)_3$—$R^1$ and a suitable base, examples of which include hydroxide and carbonate bases.

Schemes

The following schemes generally illustrate the processes of the present invention. $R^1$ $R^{1'}$, and X are not limited to the groups specifically disclosed, nor are the processes limited to the disclosed catalysts, bases, reducing agents, and enantioselective reagents.

Scheme 1

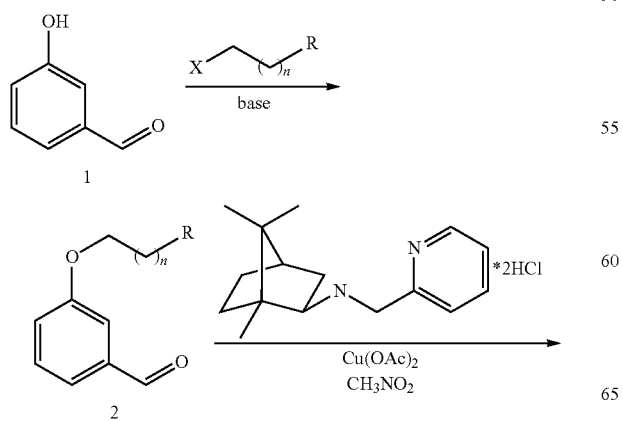

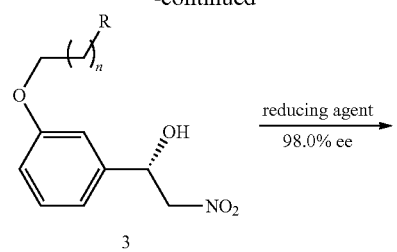

3

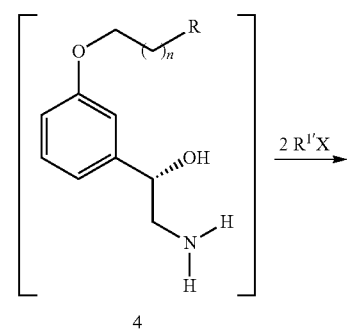

4

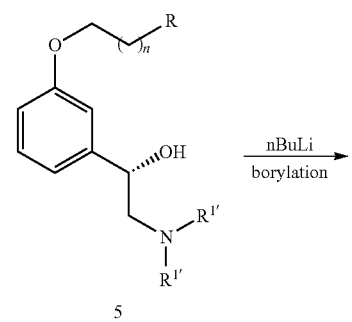

5

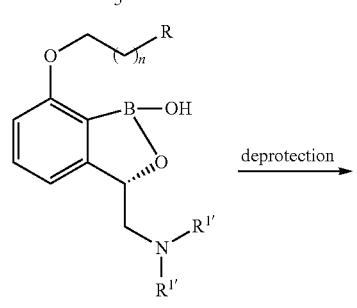

6

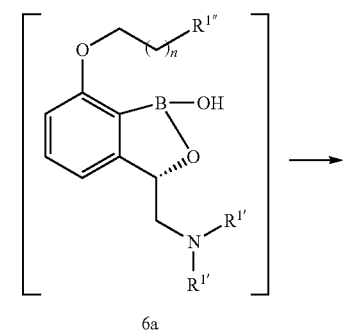

6a

-continued

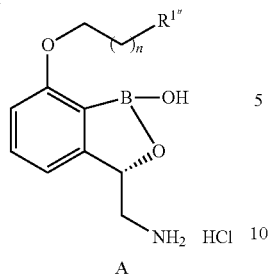

A

-continued

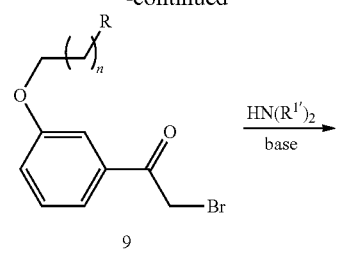

9

In accordance with Scheme 1,3-hydroxybenzaldehyde (compound 1) is contacted with $XCH_2(CH_2)_nCH_2R$ in the presence of a suitable base under conditions sufficient to form compound 2.

Compound 2 is converted to the corresponding (1S)-2-nitro-1-phenylethanol (compound 3) using nitromethane and a suitable chiral reagent such as 1,7,7-trimethyl-N-(pyridin-2-ylmethyl)bicyclo[2.2.1]heptan-2-amine di-hydrochloride; (4S)-4-ethyl-2-{1-ethyl-1-[(4S)-4-(1-methylethyl)-4,5-dihydro-1,3-oxazol-2-yl]propyl}-4,5-dihydro-1,3-oxazole; (S)-4-(tert-butyl)-2-(2-((S)-4-methyl-4,5-dihydrooxazol-2-yl)propan-2-yl)-4,5-dihydrooxazole; or N1,N2-bis[(1R,2R,4R)-1,7,7-trimethylbicyclo[2.2.1]hept-2-yl]-1,2-ethanediamine in the presence of a suitable catalyst such as $Cu(OAc)_2$. Compound 3 is then converted to the corresponding primary amine (compound 4) then protected with $R^1X$ to form compound 5; this intermediate may be isolated as the free base or as a salt, preferably the hydrochloride salt.

Compound 5 or a salt thereof is borylated with a suitable borylating reagent in the presence of a strong base such as n-BuLi, n-hexyllithium, or sec-BuLi to form Compound 6. This intermediate is deprotected to form the aminomethyl benzoxaborole, preferably (3S)-3-(aminomethyl)-7-[(3-hydroxypropyl)oxy]-2,1-benzoxaborol-1(3H)-ol. This product is advantageously isolated as a hydrochloride salt, and can be further purified by way of recrystallization.

Scheme 2

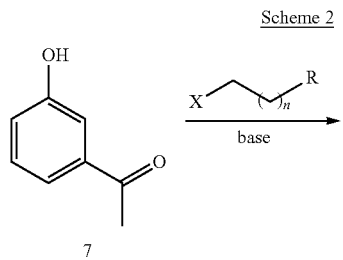

7

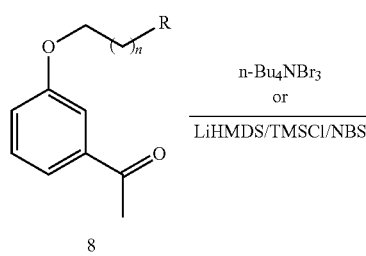

8

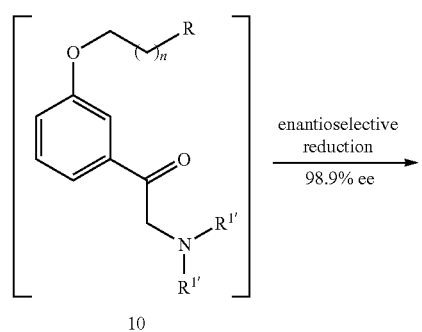

10

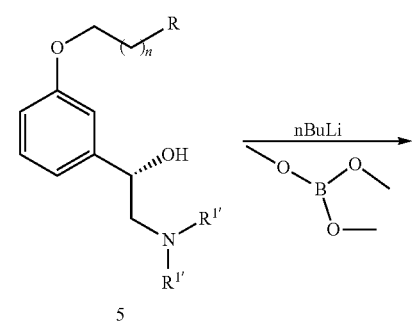

5

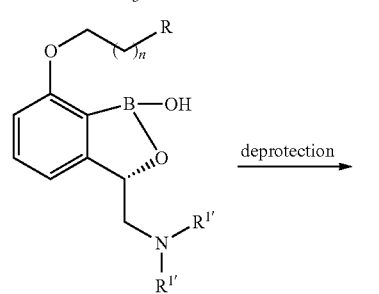

6

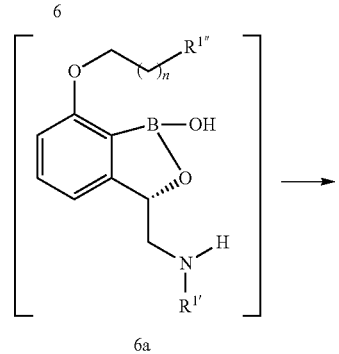

6a

-continued

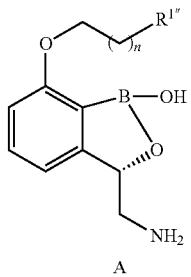

A

In accordance with Scheme 2,3-hydroxyacetophenone (compound 7) is contacted with $XCH_2(CH_2)_nCH_2$—R in the presence of a suitable base under conditions sufficient to form compound 8. Bromination with a suitable brominating reagent results in the formation of the bromoketone (compound 9), which in turn is contacted with $HN(R^1)_2$ under conditions sufficient to form the protected amine (compound 10).

Compound 10 or a salt thereof is enantioselectively reduced to the corresponding (1S)-2-amino-1-phenylethanol (Compound 5) under enantioselective reductions conditions.

Compound 5 or a salt thereof is then borylated and deprotected as described in Scheme 1 to form the aminomethyl benzoxaborole, preferably (3S)-3-(aminomethyl)-7-[(3-hydroxypropyl)oxy]-2,1-benzoxaborol-1(3H)-ol, preferably as the hydrochloride salt.

The following examples are illustrative of the process of the present invention and are not intended to limit the scope of the invention.

EXAMPLE 1

Preparation of (3S)-3-(Aminomethyl)-7-[(3-hydroxypropyl)oxy]-2,1-benzoxaborol-1(3H)-ol Hydrochloride 1A. Preparation of 3-({3-[(Phenylmethyl)oxy]propyl}oxy)benzaldehyde

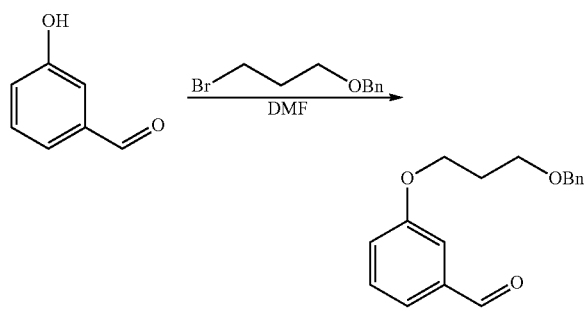

To a 3-L reaction vessel was charged and stirred cesium carbonate (209.6 g), 3-hydroxybenzaldehyde (67.6 g), dimethylformamide (DMF, 250 mL) and 3-bromopropyl phenylmethyl ether (113.4 g) at ambient temperature for ~18 h. Water (567 mL) was added followed by tert-butyl methyl ether (907 mL). The bottom aqueous layer was separated and the organic layer washed with 1N sodium hydroxide (2×567 mL) and water (1×567 mL). The organic solution was concentrated to a minimum after which ethanol (200 proof, 907 mL) was added and the solution concentrated to a minimum and filtered though a 1-μm filter.

1B. Preparation of (1S)-2-Nitro-1-[3-({3-[(phenylmethyl)oxy]propyl}oxy)phenyl]ethanol

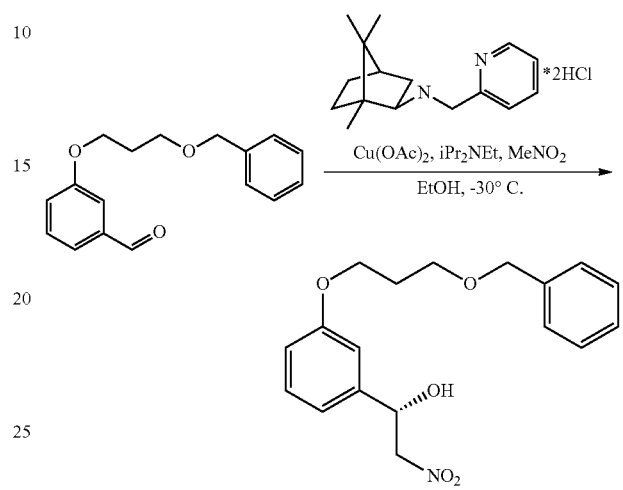

Copper (II) acetate and camphoraminomethylpyridine bis-HCl salt (504 mg) were charged to a reactor, followed by ethanol (60 mL) and diisopropylethylamine (1.16 mL). The contents were stirred for 1 h at room temperature, at which time a solution of 3-({3-[(phenylmethyl)oxy]propyl}oxy) benzaldehyde in ethanol (15 g in 15 mL) was charged. The reaction mixture was cooled to −30° C. to −40° C., whereupon nitromethane (33.9 g) was added slowly to the reaction, maintaining a temperature below −30° C., followed by diisopropylethylamine (359 mg). The reaction temperature was maintained at −30° C. for 24-48 h. When the reaction was complete, trifluoroacetic acid (952 mg) was charged to the reaction, and the contents were transferred to a separate reactor containing a room temperature solution of 1 N HCl (75 mL) and t-butyl methyl ether (TBME, 150 mL). After the addition was complete, the layers were allowed to separate and the aqueous phase removed. The organic phase was then washed with water (75 mL) and the aqueous phase removed. The solution of product in TBME was then filtered through a pad of silica gel (15 g) which was rinsed with TBME. The product was stored cold as a solution in TBME, to be swapped to ethanol prior to the subsequent hydrogenation step.

1C1. Preparation of (1S)-2-Amino-1-[3-({3-[(phenylmethyl)oxy]propyl}oxy)phenyl]ethanol

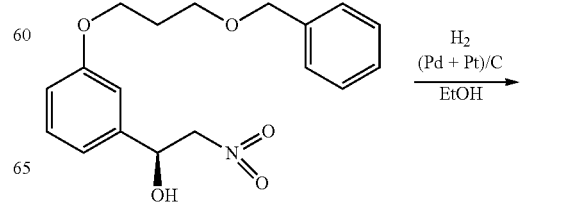

-continued

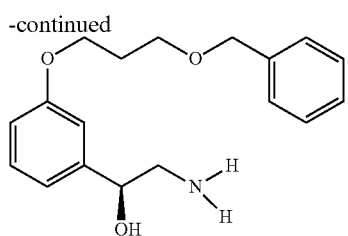

The (1S)-2-nitro-1-[3-({3-[(phenylmethyl)oxy]propyl}oxy)phenyl]ethanol in ethanol solution (8 g in 160 mL) was hydrogenated using a Pd (4%)/Pt(1%)/C catalyst (1.6 g). Upon consumption of the starting material and the hydroxylamine intermediate, the reaction product in ethanol was filtered.

1C2. Preparation of (1S)-2-[Bis(phenylmethyl)amino]-1-[3-({3-[(phenylmethyl)oxy]propyl}oxy)phenyl]ethanol hydrochloride

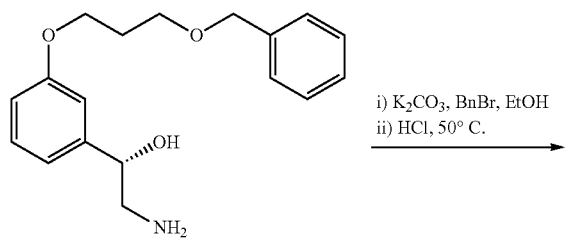

i) $K_2CO_3$, BnBr, EtOH
ii) HCl, 50° C.

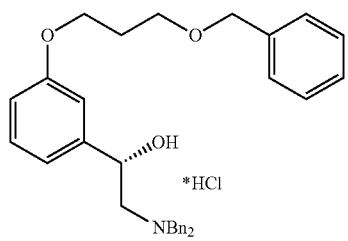

Powdered potassium carbonate (12.8 g) was charged to a 250-mL reactor, followed by the ethanolic solution of (1S)-2-amino-1-[3-({3-[(phenylmethyl)oxy]propyl}oxy)phenyl]ethanol (12.7 g in 100 mL). Additional ethanol was charged into the slurry (40 mL). Benzyl bromide (15.9 g) was charged to the reactor, and the slurry was stirred at 20-25° C. for 18 h-24 h, after which time, the solids were filtered and washed with ethanol (50 mL). The filtrate was diluted with water (50 mL) then heated to 50° C. Concentrated HCl (3.52 mL) was charged to the reactor resulting the precipitation of the HCl salt of the product. At the onset of precipitation, the slurry was held at 50° C. for 30 min, then cooled to 0° C. and held at 0° C. for an additional 30 min. The product was filtered and washed with a 0° C. solution of 20% aqueous ethanol (~60 mL).

1D. Preparation of (3S)-3-{[Bis(phenylmethyl)amino]methyl}-7-({3-[(phenylmethyl)oxy]propyl}oxy)-2,1-benzoxaborol-1(3H)-ol

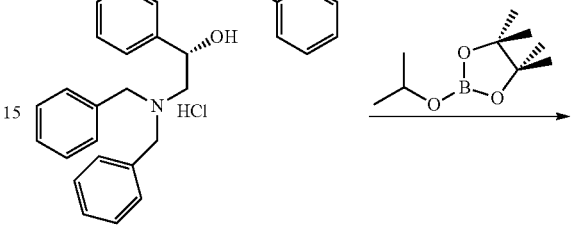

nBuLi
then
THF (0.9 volumes)
and

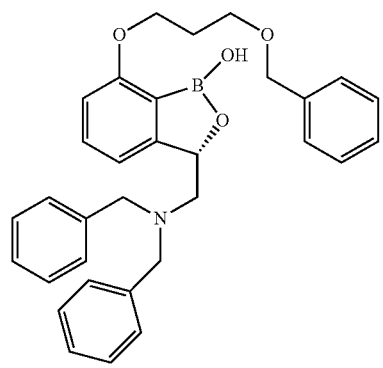

(1S)-2-[Bis(phenylmethyl)amino]-1-[3-({3-[(phenylmethyl)oxy]propyl}oxy)phenyl]ethanol hydrochloride (20 g) and toluene (160 mL) were charged into the 250-mL reactor. The contents were mixed thoroughly for about 5 min after which the mixture was degassed by placing the reactor under vacuum and backfilling with nitrogen; and repeating two times. The suspension was heated to 50-55° C., at which time nBuLi (16.3 mL, 2.6 M) was added over about 1 h with vigorous mixing. The mixture was then stirred for about 1 h at 50-55° C., at which time the starting material was observed to be consumed. The mixture was then cooled to −20 to −40° C. whereupon 1.0 equiv of nBuLi (14.8 mL) was added at such a rate to maintain the temperature to below −20° C. Upon completion of addition, the temperature was adjusted to −30 to −40° C. and nBuLi (43 mL) was added as quickly as possible (<10 minutes) while still keeping the temperature below −20° C. during addition. The temperature was adjusted to −20 to −25° C. and stirred for 1 hr. The mixture was cooled to −75 to −80° C. and an aliquot was quenched directly into $CD_3OD$. Once complete deuterium incorporation was observed, evidenced by LCMS, THF (18 mL) was added directly followed by rapid addition of the borate (36 mL). The mixture was warmed to 15-25° C. over 30 min to 1 h, 5% aq. $NaHCO_3$ (200 mL) was then added and the mixture was stirred vigorously for ~15 min. The resulting suspension was filtered and the cake rinsed with at least 30 mL of TBME. The filtrate was allowed to separate and the organic layer was then

1E. Preparation of (3S)-3-(Aminomethyl)-7-[(3-hydroxypropyl)oxy]-2,1-benzoxaborol-1(3H)-ol hydrochloride

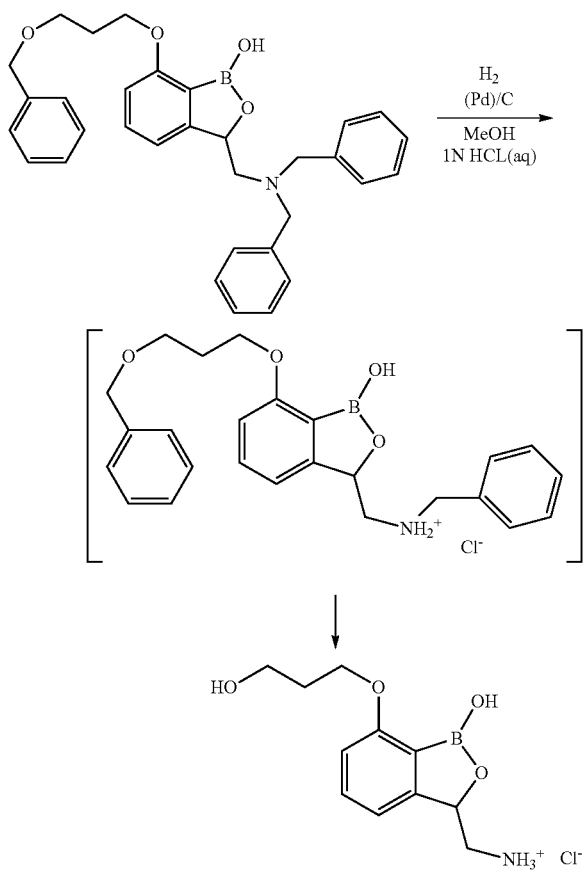

To a solution of (3S)-3-(aminomethyl)-7-[(3-hydroxypropyl)oxy]-2,1-benzoxaborol-1(3H)-ol hydrochloride in toluene (~46 mL) was added methanol (200 mL), 1 N HCl in water (42.5 mL), and 5% Pd/C catalyst (2 g, 11 wt %). The resulting mixture was treated with hydrogen gas at 100 psig and 50° C. Upon consumption of the mono N-benzyl amine intermediate, the reaction solution was filtered through a filtering aid, followed by a 1 μm filtration. The filtered solution of crude product was then distilled, 2-propanol added (200 mL), then distilled again to minimum stirrable volume. This concentrated solution was allowed to crystallize at room temperature, then filtered and washed with 2-propanol. $^1$H NMR: (d4-methanol, 400.13 MHz) d (ppm) 7.48 (t, J=7.81 Hz, 1 H), 7.01 (d, J=7.58 Hz, 1 H), 6.93 (d, J=8.21 Hz, 1 H), 5.37 (dd, J=2.76, 8.77 Hz, 1 H), 4.18 (t, J=6.11 Hz, 2 H), 3.78 (t, J=5.47 Hz, 2 H), 3.59 (dd, J=2.87, 13.29 Hz, 1 H), 2.92 (dd, J=8.86, 13.29 Hz, 1 H), 2.00 (m, J=6.13 Hz, 2 H). The accurate mass of the protonated molecule of [M+H]$^+$ was measured at m/z 238.1247 using positive ion electrospray ionization. The calculated mass of this ion is at m/z 238.1251. Chiral purity was found to be 99.9% using chiral HPLC.

EXAMPLE 2

Preparation of (3S)-3-(Aminomethyl)-7-[(3-hydroxypropyl)oxy]-2,1-benzoxaborol-1(3H)-ol Hydrochloride

2A. Preparation of 3-({3-[(Phenylmethyl)oxy]propyl}oxy)benzaldehyde

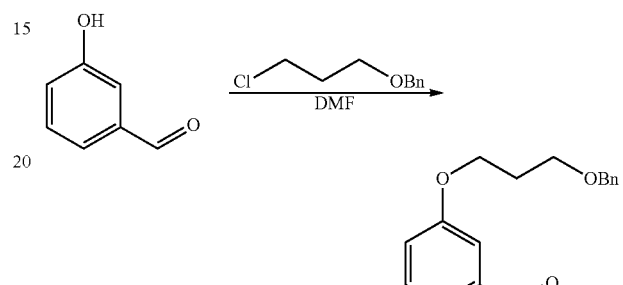

To a 3-L reaction vessel was charged and stirred potassium carbonate (152 g), 3-hydroxybenzaldehyde (67.6 g), dimethylformamide (DMF, 250 mL) and 3-chloropropyl phenylmethyl ether (96.4 g) at 90° C. for ~18 h. Water (567 mL) was added followed by tert-butyl methyl ether (907 mL). The bottom aqueous layer was separated and the organic layer washed with 1N sodium hydroxide (2×567 mL) and water (1×567 mL). The organic solution was concentrated to a minimum after which ethanol (200 proof, 907 mL) was added and the solution concentrated to a minimum and filtered though a 1-μm filter.

2B. Preparation of (1S)-2-Nitro-1-[3-({3-[(phenylmethyl)oxy]propyl}oxy)phenyl]ethanol

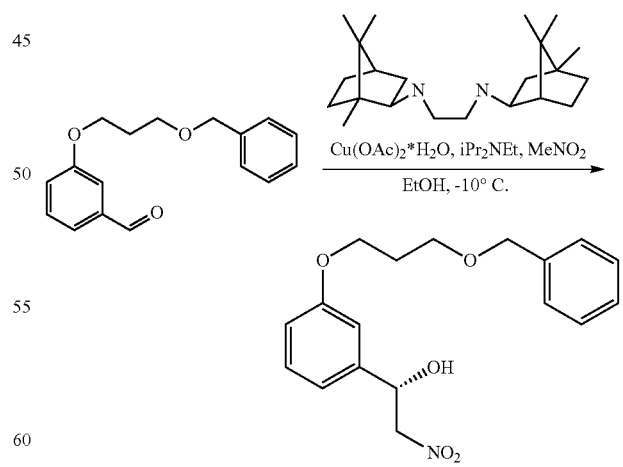

Copper (II) acetate monohydrate (3.70 g, 0.05 eq) and bis-camphorethylenediamine (N1,N2-bis[(1R,2R,4R)-1,7,7-trimethylbicyclo[2.2.1]hept-2-yl]-1,2-ethanediamine) (7.38 g, 0.06 eq) were charged to a reactor, followed by ethanol (200 mL, 2 vol). The contents were heated to 50-60° C. for ~1 h or until all solids dissolved, then cooled to room temperature and stirred, at which time a solution of 3-({3-[(phenylmethyl)oxy]propyl}oxy)benzaldehyde in ethanol (100 g, 1 eq in 50 mL, 0.5 vol) was charged. The reaction mixture was cooled to −10° C. to −20° C., whereupon nitromethane (112.7 g, 5 eq) was added slowly to the reaction, maintaining a temperature below −10° C., followed by diisopropylethylamine (1.94 mL, 1.44 g, 0.03 eq). The reaction temperature was maintained at −10° C. for ~22-30 h. When the reaction was complete, a room temperature solution of 1 N HCl (250 mL, 2.5 vol) and t-butyl methyl ether (TBME, 500 mL, 5 vol) were charged to the reaction vessel. Following the addition, the contents were stirred for ~5 minutes and brought to 20° C. (~room temperature), and then the layers were allowed to separate and the aqueous phase removed. The organic phase was then washed 2× with water (250 mL, 2.5 vol) and each time the aqueous phase removed. TBME was then distilled off and replaced with absolute ethanol.

2C1. Preparation of (1S)-2-Amino-1-[3-({3-[(phenylmethyl)oxy]propyl}oxy)phenyl]ethanol

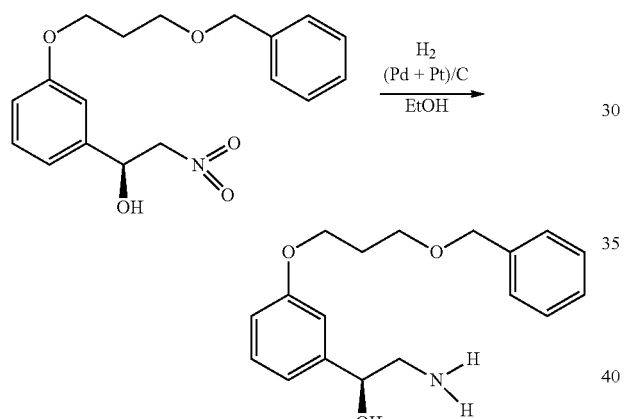

The (1S)-2-nitro-1-[3-({3-[(phenylmethyl)oxy]propyl}oxy)phenyl]ethanol in ethanol solution (8 g in 160 mL) was hydrogenated using a Pd (4%)/Pt(1%)/C catalyst (1.6 g). Upon consumption of the starting material and the hydroxylamine intermediate, the reaction product in ethanol was filtered.

2C2. Preparation of (1S)-2-[Bis(phenylmethyl)amino]-1-[3-({3-[(phenylmethyl)oxy]propyl}oxy)phenyl]ethanol hydrochloride

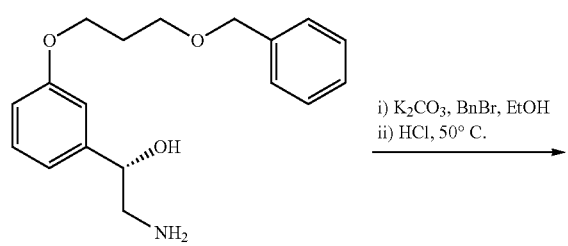

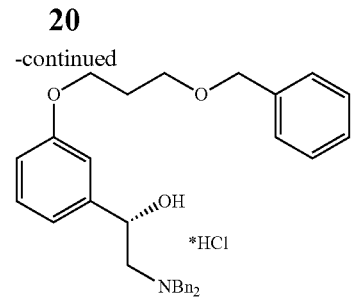

Powdered potassium carbonate (12.8 g) was charged to a 250-mL reactor, followed by the ethanolic solution of (1S)-2-amino-1-[3-({3-[(phenylmethyl)oxy]propyl}oxy)phenyl]ethanol (12.7 g in 100 mL). Additional ethanol was charged into the slurry (40 mL). Benzyl bromide (15.9 g) was charged to the reactor, and the slurry was stirred at 20-25° C. for 18 h-24 h, after which time, the solids were filtered and washed with ethanol (50 mL). The filtrate was diluted with water (50 mL) then heated to 50° C. Concentrated HCl (3.52 mL) was charged to the reactor resulting the precipitation of the HCl salt of the product. At the onset of precipitation, the slurry was held at 50° C. for 30 min, then cooled to 0° C. and held at 0° C. for an additional 30 min. The product was filtered and washed with a 0° C. solution of 20% aqueous ethanol (~60 mL).

2D. Preparation of (3S)-3-{[Bis(phenylmethyl)amino]methyl}-7-({3-[(phenylmethyl)oxy]propyl}oxy)-2,1-benzoxaborol-1(3H)-ol

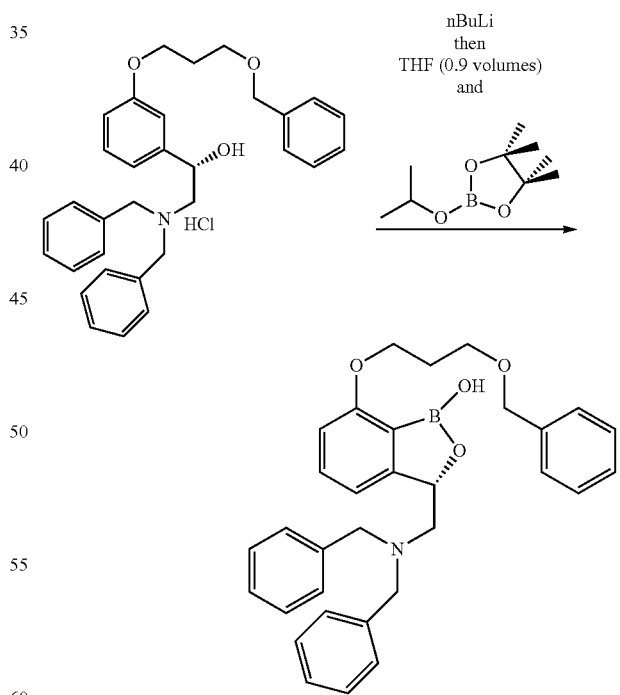

(1S)-2-[Bis(phenylmethyl)amino]-1-[3-({3-[(phenylmethyl)oxy]propyl}oxy)phenyl]ethanol hydrochloride (20 g) and toluene (160 mL) were charged into the 250-mL reactor. The contents were mixed thoroughly for about 5 min after which the mixture was degassed by placing the reactor under vacuum and backfilling with nitrogen; and repeating two times. The suspension was heated to 50-55° C., at which time nBuLi (16.3 mL, 2.6 M) was added over about 1 h with vigorous mixing. The mixture was then stirred for about 1 h at 50-55° C., at which time the starting material was observed to be consumed. The mixture was then cooled to −20 to −40° C. whereupon 1.0 equiv of nBuLi (14.8 mL) was added at such a rate to maintain the temperature to below −20° C. Upon completion of addition, the temperature was adjusted to −30 to −40° C. and nBuLi (43 mL) was added as quickly as possible (<10 minutes) while still keeping the temperature below −20° C. during addition. The temperature was adjusted to −20 to −25° C. and stirred for 1 hr. The mixture was cooled to −75 to −80° C. and an aliquot was quenched directly into $CD_3OD$. Once complete deuterium incorporation was observed, evidenced by LCMS, THF (18 mL) was added directly followed by rapid addition of the borate (36 mL). The mixture was warmed to 15-25° C. over 30 min to 1 h, 5% aq. $NaHCO_3$ (200 mL) was then added and the mixture was stirred vigorously for ~15 min. The resulting suspension was filtered and the cake rinsed with at least 30 mL of TBME. The filtrate was allowed to separate and the organic layer was then washed three or four times with water (100 mL), allowing the last wash at least 1 h to settle. The organic layer was concentrated to about 40 mL.

2E. Preparation of (3S)-3-(Aminomethyl)-7-[(3-hydroxypropyl)oxy]-2,1-benzoxaborol-1(3H)-ol hydrochloride

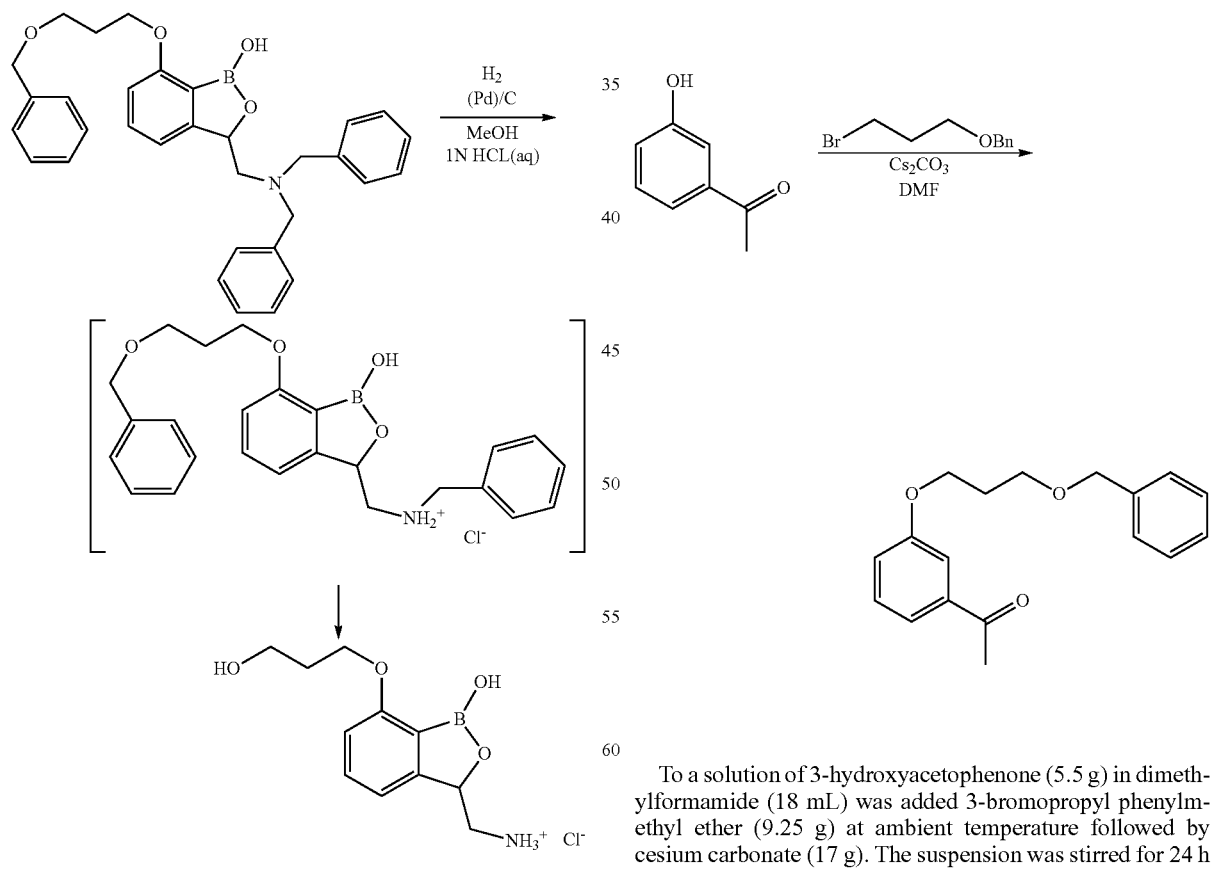

To a solution of (3S)-3-(aminomethyl)-7-[(3-hydroxypropyl)oxy]-2,1-benzoxaborol-1(3H)-ol hydrochloride in toluene (~46 mL) was added methanol (200 mL), 1 N HCl in water (42.5 mL), and 5% Pd/C catalyst (2 g, 11 wt %). The resulting mixture was treated with hydrogen gas at 100 psig and 50° C. Upon consumption of the mono N-benzyl amine intermediate, the reaction solution was filtered through a filtering aid, followed by a 1 μm filtration. The filtered solution of crude product was then distilled, 2-propanol added (200 mL), then distilled again to minimum stirrable volume. This concentrated solution was allowed to crystallize at room temperature, then filtered and washed with 2-propanol. $^1$H NMR: (d4-methanol, 400.13 MHz) d (ppm) 7.48 (t, J=7.81 Hz, 1 H), 7.01 (d, J=7.58 Hz, 1 H), 6.93 (d, J=8.21 Hz, 1 H), 5.37 (dd, J=2.76, 8.77 Hz, 1 H), 4.18 (t, J=6.11 Hz, 2 H), 3.78 (t, J=5.47 Hz, 2 H), 3.59 (dd, J=2.87, 13.29 Hz, 1 H), 2.92 (dd, J=8.86, 13.29 Hz, 1 H), 2.00 (m, J=6.13 Hz, 2 H). The accurate mass of the protonated molecule of $[M+H]^+$ was measured at m/z 238.1247 using positive ion electrospray ionization. The calculated mass of this ion is at m/z 238.1251. Chiral purity was found to be 99.9% using chiral HPLC.

EXAMPLE 3

Alternative Preparation of (3S)-3-(Aminomethyl)-7-[(3-hydroxypropyl)oxy]-2,1-benzoxaborol-1(3H)-ol Hydrochloride 3A. Preparation of 1-[3-({3-[(Phenylmethyl)oxy]propyl}oxy)phenyl]ethanone To a solution of 3-hydroxyacetophenone (5.5 g) in dimethylformamide (18 mL) was added 3-bromopropyl phenylmethyl ether (9.25 g) at ambient temperature followed by cesium carbonate (17 g). The suspension was stirred for 24 h and water was added followed by ethyl acetate. The organic layer was separated and the aqueous layer extracted with ethyl acetate. The organic layers were combined and washed twice with 2 N sodium hydroxide, four times with brine, and concentrated in vacuo to an oil to give the title compound.

3B. Preparation of 2-Bromo-1-[3-({3-[(phenylmethyl)oxy]propyl}oxy)phenyl]ethanone

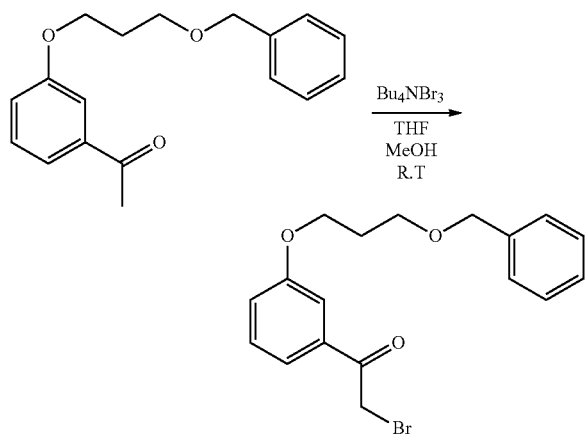

To a solution of 1-[3-({3-[(phenylmethyl)oxy]propyl}oxy)phenyl]ethanone (10.59 g) in tetrahydrofuran (50 mL) was added methanol (50 mL) and a solution of tetrabutylammonium tribromide (16 g) in tetrahydrofuran (50 mL). The reaction was stirred at ambient temperature for 45 min at which time tetrabutylammonium tribromide (0.89 g) was added, followed by further addition of 0.6 g. 10% aqueous sodium thiosulfate was added to the reaction and the mixture was concentrated in vacuo to a minimum volume. Ethyl acetate was added and the resultant organic solution was washed with aqueous sodium thiosulfate, saturated sodium bicarbonate and brine and concentrated to an oil to afford the title compound.

3C. Preparation of 2-[Bis(phenylmethyl)amino]-1-[3-({3[(phenylmethyl)oxy]propyl}oxy)phenyl]ethanone

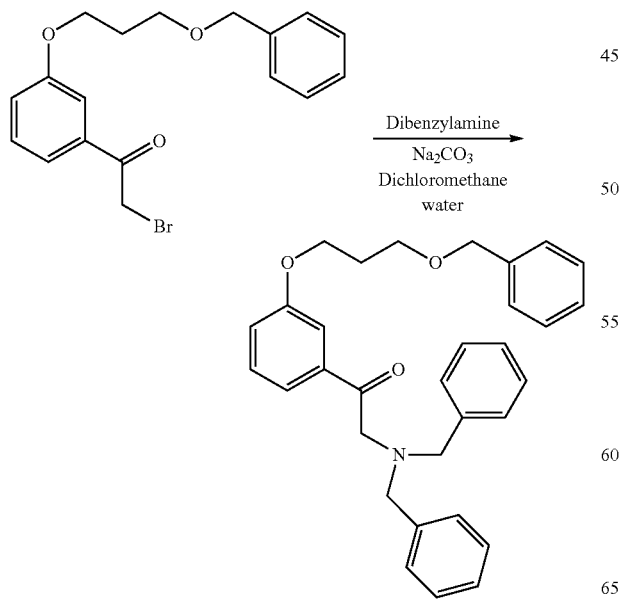

To a mixture of 2-bromo-1-[3-({3-[(phenylmethyl)oxy]propyl}oxy)phenyl]ethanone (13.17 g), dibenzylamine (6.4 g) and dichloromethane (25 mL) was added a solution of sodium carbonate (7.6 g) in water (50 mL). The reaction mixture was stirred at ambient temperature overnight. The organic layer was separated and concentrated to a minimum and tert-butyl methyl ether was added. The organic layer was washed with dilute acetic acid (4 times) and 0.1N sodium hydroxide once and brine once. The organic solution was concentrated to dryness. The oil was washed with methanol and purified by chromatography to give the title compound.

3D: Preparation of (1S)-2-[bis(phenylmethyl)amino]-1-[3-({3-[(phenylmethyl)oxy]propyl}oxy)phenyl]ethanol

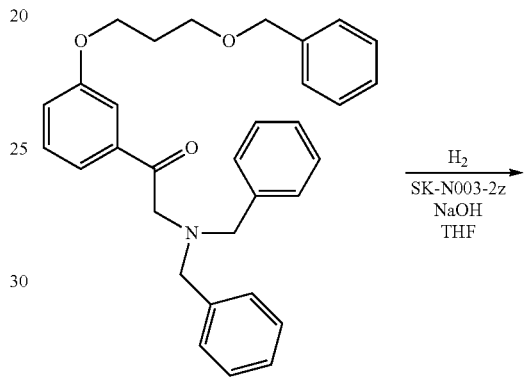

A mixture of 2-[bis(phenylmethyl)amino]-1-[3-({3[(phenylmethyl)oxy]propyl}oxy)phenyl]-ethanone, catalyst SK-N003-2z (Naud catalyst, 47 mg) and 1M sodium hydroxide (2.085 mL) in tetrahydrofuran (10 mL) was set under hydrogen at 150 psi for 4 h. The reaction mixture was then filtered through silica gel. The crude filtrate was purified by chromatography eluting with tert-butyl methyl ether-hexane (0-60%) to yield the desired product as a yellow oil.

3E: Preparation of (3S)-3-{[bis(phenylmethyl)amino]methyl}-7-({3-[(phenylmethyl)oxy]propyl}oxy)-2,1-benzoxaborol-1(3H)-ol

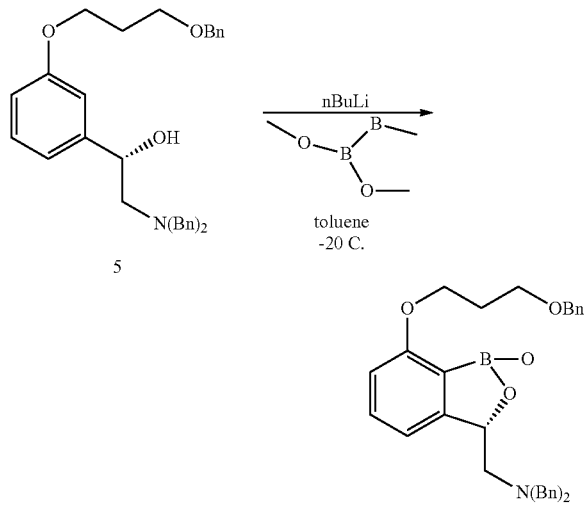

To a solution of (1S)-2-[bis(phenylmethyl)amino]-1-[3-({3-[(phenylmethyl)oxy]propyl}oxy)phenyl]ethanol (240 mg, 0.50 mmol) in 5 mL of toluene at −20° C. was added 1.75 mmol of nBuLi in hexane (2.59 M, 0.67 mL) over about 5 minutes. The mixture was then stirred for 2 h and then quenched with freshly distilled trimethylborate (0.28 mL, 259 mg, 2.5 mmol). The cold bath was removed and the mixture warmed to room temperature. The reaction was then diluted with 10 mL of TBME, then 5 mL of saturated NaHCO$_3$ solution was added. After vigorously stirring for about 30 min, the organic layer was washed with 5 mL of 0.1 M NaH$_2$PO$_4$, then 5 mL of saturated NaHCO$_3$. The organic layer was then dried over Na$_2$SO$_4$ and concentrated.

The invention claimed is:

1. A process comprising contacting a compound of formula 6:

6

[structure]

or a pharmaceutically acceptable salt thereof; with a deprotecting reagent that is a reducing reagent, wherein the reducing agent is provided in the presence of HCl to form the hydrochloride salt of a compound of formula A:

A

[structure]

and

—where R is OR$^1$; R$^1$ and each R$^1$ are each independently benzyl groups; R$^{1'}$ is H or OH; and n is 1.

2. The process of claim 1 wherein the deprotecting reagent is Pd/C or Pt/C in the presence of H$_2$ or a mixture thereof, H$_2$ over palladium hydroxide, or catalytic transfer hydrogenating reagent ammonium formate and Pd/C.

3. The process of claim 1 wherein the compound of formula 6 is prepared by contacting a compound of formula 5:

5

[structure]

or a salt thereof with a borylating reagent characterized by the following formula:

$$R^3\!-\!O\!-\!\underset{\underset{OR^2}{|}}{B}\!-\!OR^2$$

in the presence of an alkyllithium reagent, where each R$^2$ is independently C$_1$-C$_6$-alkyl, or together with the oxygen atoms to which they are attached form a 5- or 6-membered ring; and R$^3$ is C$_1$-alkyl, C$_2$-alkyl, C$_3$-alkyl, C$_4$-alkyl, C$_5$-alkyl, C$_6$-alkyl.

4. The process of claim 3 wherein the borylating reagent is isopropylpinacolborate, or a tri-C$_1$-borate, tri-C$_2$-borate or tri-C$_3$-borate; n is 1; and the alkyl lithium reagent is n-BuLi, n-hexyllithium, or sec-BuLi.

5. The process of claim 3 wherein the borylating reagent is isopropylpinacolborate or trimethyl borate; n is 1 and the alkyl lithium reagent is n-BuLi.

6. The process of claim 3 wherein the compound of formula 5 or a salt thereof is prepared either by enantioselective reduction of a compound of formula 10

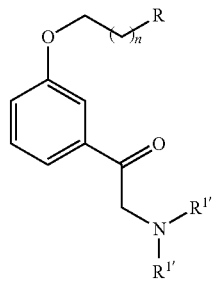

or a salt thereof;
or by contacting under basic conditions R¹X with a compound of formula 4:

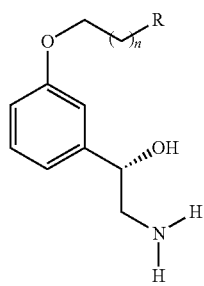

or a salt thereof,
where X is a leaving group.

7. The process of claim 6 wherein the compound of formula 5 or a salt thereof is prepared by enantioselective reduction of a compound of formula 10 using $H_2$ and Naud catalyst or $H_2$ and Noyori catalyst; and n is 1.

8. The process of claim 6 wherein the compound of formula 5 or a salt thereof is prepared by contacting the compound of formula 4 or a salt thereof with benzyl bromide in the presence of a carbonate or a hydroxide.

9. The process of claim 8 wherein the compound of formula 4 or a salt thereof is prepared by contacting formula 2:

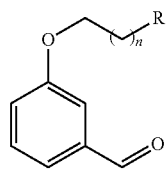

with nitromethane in the presence of a chiral reagent, to form a compound of formula 3:

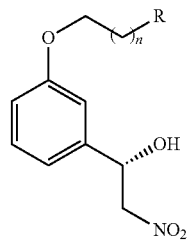

then reducing the nitro group to an amine group.

10. The process of claim 9 wherein the chiral reagent is 1,7,7-trimethyl-N-(pyridin-2-ylmethyl)bicyclo[2.2.1]heptan-2-amine di-hydrochloride; (4S)-4ethyl-2-{1-ethyl-1-[(4S)-4-(1-methylethyl)-4,5-dihydro-1, 3-oxazol-2-yl]propyl}-4,5-dihydro-1, 3-oxazole; (S)-4-(tert-butyl)-2-(2-((S)-4-methyl-4,5-dihydrooxazol-2-yl)propan-2-yl)-4,5-dihydrooxazole; or N1,N2-bis[(1R,2R,4R)-1,7,7-trimethylbicyclo[2.2.1]hept-2-yl]-1,2-ethanediamine and $Cu(OAc)_2$; and n is 1.

11. The process of claim 6 wherein the compound of formula 10 or a salt thereof is prepared by contacting $HN(R^1)_2$ with a base and a compound of formula 9:

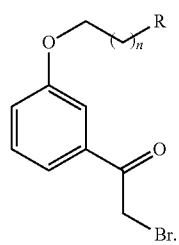

12. The process of claim 11 wherein the compound of formula 9 is prepared by bromination of a compound of formula 8:

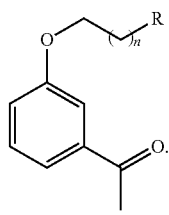

13. A process comprising the steps of:
a) contacting a compound of formula 2:

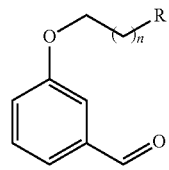

with nitromethane in the presence of a chiral reagent to make a compound of formula 3:

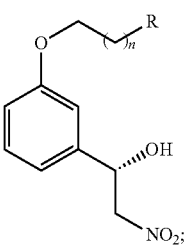

where R is H or OR¹; R¹ is a protecting group; and n is 0, 1, 2, 3, 4 or 5;

b) reducing the compound of formula 3 to form a compound of formula 4:

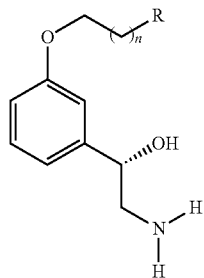

or a salt thereof;

c) contacting the compound of formula 4 or a salt thereof with R¹'X with a base to form a compound of formula 5:

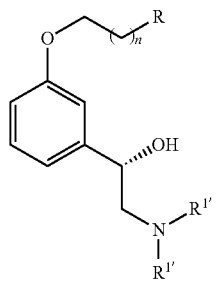

or a salt thereof,
wherein R¹' is a protecting group and X is a leaving group;

d) contacting the compound of formula 5 or a salt thereof with a borylating reagent characterized by the following formula:

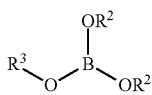

in the presence of n-BuLi to form a compound of formula 6:

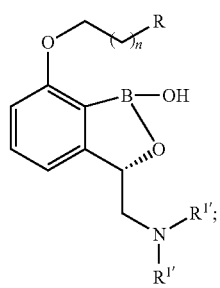

or a pharmaceutically acceptable salt thereof,
where each R² is independently C₁-alkyl, C₂-alkyl, C₃-alkyl, C₄-alkyl, C₅-alkyl, C₆-alkyl, or together with the oxygen atoms to which they are attached form a 5- or 6-membered ring; and R³ is C₁-alkyl, C₂-alkyl, C₃-alkyl, C₄-alkyl, C₅-alkyl, C₆-alkyl; and e) contacting the compound of formula 6 or a pharmaceutically acceptable salt thereof with a deprotecting reagent to form a compound of formula A or a pharmaceutically acceptable salt thereof:

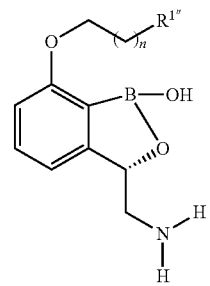

where R¹" is H or OH.

14. The process of claim 13 wherein:
R¹ and each R¹' are benzyl groups;
n is 0, 1, 2, or 3;
the chiral reagent is Cu(OAc)₂ and 1,7,7-trimethyl-N-(pyridin-2-ylmethyl)bicyclo[2.2.1]heptan-2-amine di-hydrochloride; (4S)-4-ethyl-2-{1-ethyl-1-[(4S)-4-(1-methylethyl)-4,5-dihydro-1,3-oxazol 2-yl]propyl1-4,5-dihydro-1,3-oxazole; (S)-4-(tert-butyl)-2-(2-((S)-4-methyl-4,5-dihydrooxazol-2yl)propan-2-yl)-4,5-dihydrooxazole; or N1,N2-bis[(1R,2R,4R)-1,7,7-trimethylbicyclo[2.2.1]hept-2yl]-1,2-ethanediamine;
X is a leaving group selected from Br, Cl, I, tosyl or triflyl;
the borylating reagent is isopropylpinacolborate or trimethylborate; and
the deprotecting agent is hydrogenation in the presence of a Pd/C catalyst, Pt/C catalyst or a mixture of Pd/C +Pt/C catalysts.

15. A process comprising the steps of:
a) brominating a compound of formula 8:

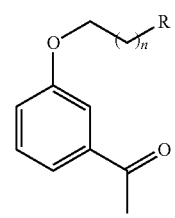

to form a compound of formula 9:

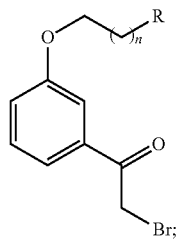

where R is H or OR'; R¹ is a protecting group; and n is 0, 1, 2, 3, 4 or 5;

b) contacting the compound of formula 9 with $HN(R^{1'})_2$ to form a compound of formula 10:

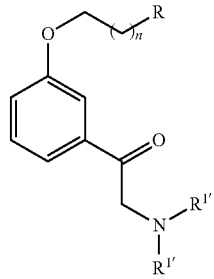

10 or a salt thereof,
where each $R^{1'}$ is a protecting group;
c) enantioselectively reducing the compound of formula 10 or a salt thereof to form a compound of formula 5:

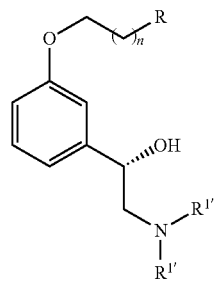

5 or a salt thereof;
d) contacting the compound of formula 5 or a salt thereof with a borylating reagent characterized by the following formula:

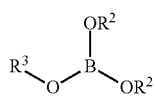

in the presence of n-BuLi, to form a compound of formula 6:

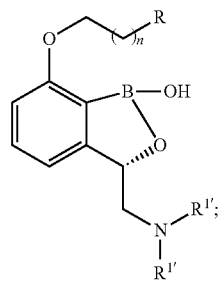

6 or a pharmaceutically acceptable salt thereof,
where each $R^2$ is independently $C_1$-alkyl, $C_2$-alkyl, $C_3$-alkyl, $C_4$-alkyl, $C_5$-alkyl, $C_6$-alkyl, or together with the oxygen atoms to which they are attached form a 5- or 6-membered ring; and
$R^3$ is $C_1$-alkyl, $C_2$-alkyl, $C_3$-alkyl, $C_4$-alkyl, $C_5$-alkyl, $C_6$-alkyl; and
e) contacting the compound of formula 6 or a pharmaceutically acceptable salt thereof with a deprotecting reagent to form a compound of formula A or a pharmaceutically acceptable salt thereof:

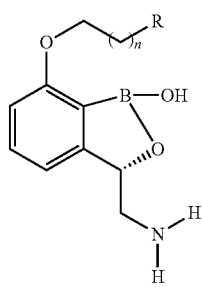

A where $R^{1'''}$ is H or OH.

\* \* \* \* \*